US006318996B1

United States Patent
Melikechi et al.

(10) Patent No.: US 6,318,996 B1
(45) Date of Patent: Nov. 20, 2001

(54) METHOD FOR CURING A DENTAL COMPOSITION USING A LIGHT EMITTING DIODE

(76) Inventors: Noureddine Melikechi, 275 Merion Rd., Dover, DE (US) 19904; Ranjit Dinkar Pradhan, 200-A Grant St., Wyoming, DE (US) 19934

(*) Notice: Subject to any disclaimer, the term of this patent is extended or adjusted under 35 U.S.C. 154(b) by 0 days.

(21) Appl. No.: 09/412,683

(22) Filed: Oct. 5, 1999

(51) Int. Cl.[7] .................................................. A61C 1/00
(52) U.S. Cl. .................................................. 433/29; 362/119
(58) Field of Search .............................. 433/29; 362/119; 250/504 H

(56) References Cited

U.S. PATENT DOCUMENTS

| 4,112,335 | 9/1978 | Gonser | 315/241 H |
|---|---|---|---|
| 4,229,658 | 10/1980 | Gonser | 250/504 H |
| 4,385,344 | 5/1983 | Gonser | 362/32 |
| 5,147,204 | 9/1992 | Patten et al. | 433/229 |
| 5,420,768 | 5/1995 | Kennedy | 362/119 |
| 5,634,711 | 6/1997 | Kennedy et al. | 362/119 |
| 5,711,665 * | 1/1998 | Adam et al. | 433/29 |
| 5,885,082 | 3/1999 | Levy | 433/215 |
| 6,102,696 | 8/2000 | Osterwalder et al. | 433/29 |

OTHER PUBLICATIONS

Pilo et al; Abstract, "A Survey Of Output Intensity And Potential For Depth Of Cure Among Light–Curing Units In Clinical Use.", J Dent Mar. 1999;27(3):253–41.

Burke et al; Abstract, "Effectiveness of Light–Curing Units in Vocational Training Practices.", Prim Dent Care Sep. 1997;4(3):91–4.

Tanoue et al; Abstract, "Curing Depth of Four Composite Veneering Materialized Polymerized with Different Laboratory Photo–Curing Units.", J Oral Rehabil May 1998;25(5):358–352.

Matsumura et al; Abstract, "The Influence of Ultraviolet Radiation Intensity on Curing Depth of Photo–Activated Composite Veneering Materials." , J Oral Rehabil Oct. 1998;25(10):770–5.

* cited by examiner

Primary Examiner—John J. Wilson
(74) Attorney, Agent, or Firm—Leland K. Jordan

(57) ABSTRACT

A dental composition curing method and device for exposing a dental composition to a beam of radiation emitted by a light-emitting-diode (LED) positioned proximate the composition, LED radiation being more efficient than the conventional use of filtered white light or laser radiation.

2 Claims, 4 Drawing Sheets

METHOD FOR CURING A DENTAL COMPOSITION USING A LIGHT EMITTING DIODE

BACKGROUND OF THE INVENTION

1. Field of the Invention

The present invention relates to curing photo-curable dental compositions. In particular, the present invention provides a method to cure dental compositions using a light-emitting diode (LED) as a source of curing radiation placed proximate to the composition to be cured.

2. Description of the Related Art

Certain polymeric materials useful in the field of dentistry for adhesion, sealing and restoration may be cured or hardened upon exposure to a source of radiation. Such photoactive materials are known as "photo-curable dental compositions" and generally harden when exposed to radiation having wavelengths in the visible range. Photo-cured dental compositions are convenient for use by a dentist because the curing process can be initiated when the dental composition has been accurately placed in its proper position. A source of radiation energy positioned proximate to the material to be hardened, for example an appropriate amount of composition placed inside a tooth cavity, is activated to initiate polymerization and subsequent curing of the composition to secure the repair.

Photo-cured dental compositions were initially hardened by the application of concentrated beams of ultraviolet (UV) radiation. In order to provide such UV radiation, dental guns and other apparatuses for producing concentrated beams of UV radiation were developed. See U.S. Pat. Nos. 4,112,335 and 4,229,658, for example. Later, visible light curable dental compositions were used and dental radiation guns for producing concentrated visible light were provided like that that disclosed in U.S. Pat. No. 4,385,344. However, a relatively high divergence about 25 degrees of the light beam from such visible light sources reduces penetration into the tooth structure, leading to their relative inefficiency and unreliability for photo-curing dental composition that are thicker than about two millimeters.

Photo-curable dental materials have also been developed that are hardened by exposure to radiant energy in a preselected spectral range. Typically, a photo-activated chemical reaction in many photo-curable dental materials is initiated by application of a high intensity blue light having a wavelength of 400–500 nanometers. Since the light sources employed typically produce the entire visible light spectrum as well as some non-visible radiation, a reflector is coated to reflect only visible light, and the filters are selected to substantially block non-visible radiation and visible light other than blue light in the range of 400–500 nanometers, in order to produce the desired range of radiation, as shown for example in U.S. Pat No. 5,147,204. Laser-based radiation sources have also been employed, using for example, a Nd YAG laser producing radiation at a wavelength of about 1060 nanometers, in combination with a frequency doubling material as disclosed for example in U.S. Pat. No. 5,885,082. In the instance that a laser source is used, the beam must be de-focussed to cover the area being cured and this is done by varying by hand the distance between the dental composition and the laser dental gun.

There are several disadvantages in using light curing apparatuses of the prior art like those discussed above. Commercially available dental light guns often include an elongated, slender light guide such as a bundle of optical fibers having a free end that can be positioned close to the photo-curable material in order to direct light to the material from a light source located outside the oral cavity. Thus, because of the relatively large size of the dental gun within a patient's mouth, a degree of physical discomfort is introduced to the patient as well as to the dentist who must hold the gun steady for about one minute.

Second, the area illuminated by conventional blue-filtered metal-halide radiation is usually in the range of about a ½-inch diameter circle and over a typical curing cycle of about 60 seconds. The relatively high energy output and beam divergence of such dental guns leads to the possibility of increased heating of the pulp tissue which is sensitive to small changes in temperature.

In addition, when dental compositions are cured in place within a cavity for instance, after curing an amount of shrinkage of about 2.5% occurs leaving a gap within the area being treated; such shrinkage is so deleterious that any small reduction in shrinkage is desirable.

Furthermore, in tests of cure depth uniformity of standardized compositions, it was found that a high percentage (46%) of curing lights used in private dental offices are unsuitable for use when tested against manufacture's recommendations using a curing radiometer or a heat radiometer, due in part to the loss of output of the light source in use [J Dent March199 ;27(3):235–41]. Finally, due to the expenses of combining a laser or metal-halide radiation source, focussing elements, power sources, etc., significant expense are involved in purchasing and using dental guns. Conventional dental curing devices are therefore seen to have shortcomings including uncomfortable use, unreliable curing and relatively high expense.

U.S. Pat. No. 4,385,344 discloses a dental gun device for production of light in the low visible range for photo-curing dental compositions, the device comprising a tungsten halogen lamp with a concentrating reflector which reflects visible light and passes middle and far infrared wavelengths. A dichroic heat reflecting filter which passes light from 400 to 700 nm and reflects energy in the visible red and near infrared wavelengths back to the lamp envelope, enhances lamp halogen cycle efficiency. The dichroic heat reflecting filter is followed by a dielectric filter which provides a high efficiency bandpass at the desired visible range. A fiber optic light guide is positioned to receive the focused and filtered light and to transmit it to a reduced surface light applying tip at the end of the handpiece. The fiber light guide is encased in a specially designed sheathing which provides protection to the optical fibers and carries two electrical conductors which are connected between a control switch on the handpiece and the power supply for the lamp.

U.S. Pat. No. 5,147,204 is representative of conventional blue-light filtered dental guns. This patent discloses a blue light emitting apparatus for curing photo-curable dental material including a handpick having a housing, a depending handle and a detachable light guide. The light guide is received in a head connected to the housing. A source of tungsten-halogen light is coupled to the housing, and a light guide is detachably connected to the head for communication with the source of light. Since the tungsten-halogen light produces the entire visible light spectrum as well as some non-visible radiation, a reflector is coated to generally reflect only visible light, and a blue-pass filter and a heat filter are selected to substantially block non-visible radiation and visible light other than blue light in the range of 400–500 nanometers.

U.S. Pat. No. 5,885,082 is representative of the use of pulsed laser radiation having a selected wavelength for performing a variety of dental procedures, including curing and hardening of a dental composition containing hydroxyapatite and phosphoric acid. The use of laser radiation for curing employs a housing provided with an optical fiber coupled to a source of monochromatic light, such as an Nd YAG laser operating at a wavelength of 1060 nanometers. The optical fiber directs light radiation onto a curved mirror which deflects the radiation onto the receiving end of a further optical fiber. A frequency doubling material influences the laser radiation so that such a laser-based dental gun has the capability of applying either 1060 nanometers or 532 nanometers radiation to the area to be treated. It is significant that cooling water is disclosed as being sprayed onto the tooth in the vicinity of the spot which is being irradiated, especially when radiation at 532 nanometers is applied. A further disadvantage of the use of laser radiation is de-focussing the laser beam to be coextensive with the surface of filling composition by varying by hand the spacing between the laser dental gun and the tooth surface.

Accordingly, from a study of the different approaches taken in the prior art to the problems presented by the necessity for reliably providing a minimum essential amount of curing radiation without undue heating or other discomfort to a patient or dentists, there remains a need for an improved approach to dental polymer curing that is compatible with existing polymeric compositions and which involves smaller, easier to use and less expensive devices that operate with a smaller amount of applied radiation energy, yielding lower temperatures, and less composition shrinkage. A further need is the availability of a light source that has insignificant loss of output during use.

BRIEF SUMMARY OF THE INVENTION

The disadvantages discussed above within the prior art may be fully or at least partially overcome by using the apparatus and methods of this invention. A dental composition curing method has been developed that consists of exposing the dental composition to be hardened to radiation from a light emitting diode having output wavelengths selected to photo-activate a hardening chemical reaction within the target composition. The inventors have surprisingly discovered that the radiation beam from an LED provides the same depth of cure as achieved by a conventional blue-light filtered dental gun, even though the LED irradiation intensity is between about 50% to 80% lower for the same exposure time. In particular, to achieve a 1.5 mm depth of cure, an energy density of about 25 mW/cm$^2$ at the target composition is required for an LED-based dental gun vs. an energy density of about 53 mW/cm$^2$ required for a conventional blue-light dental gun. Remarkably, in the instance of a 2 mm depth of cure, an energy density of about only 38 mW/cm$^2$ at the target composition is required for an LED-based dental gun vs. about 200 mW/cm$^2$ required for a conventional blue-light dental gun.

Even more unexpectedly, it has been discovered that the amount of shrinkage that occurs during the curing process is about 7% lower when an LED-based dental gun of the present invention is employed instead of a conventional blue light dental gun. In addition, the smaller size of an LED permits a smaller dental gun to be employed so that the level of thermal discomfort experienced by a patient is decreased. Even further, for irradiation intensities yielding a 1.5 mm depth of cure, the degree of heating has been measure and found to be about 8% less when the LED-based dental gun of the present invention is employed instead of a conventional blue light dental gun. Even furthermore, the failure mode of operation with an LED is catastrophic in nature so that energy output remains essentially constant during use. Thus, the present dental composition curing method using a low-cost LED radiation source is more efficient for affecting dental composition curing than the conventional use of filtered white light or laser radiation, thereby providing significant benefits to both dentist and patient alike.

BRIEF DESCRIPTION OF THE DRAWINGS

The invention will be more fully understood from the following detailed description thereof taken in connection with the accompanying drawings which form a part of this application and in which.

DETAILED DESCRIPTION OF THE INVENTION

Figure 1:
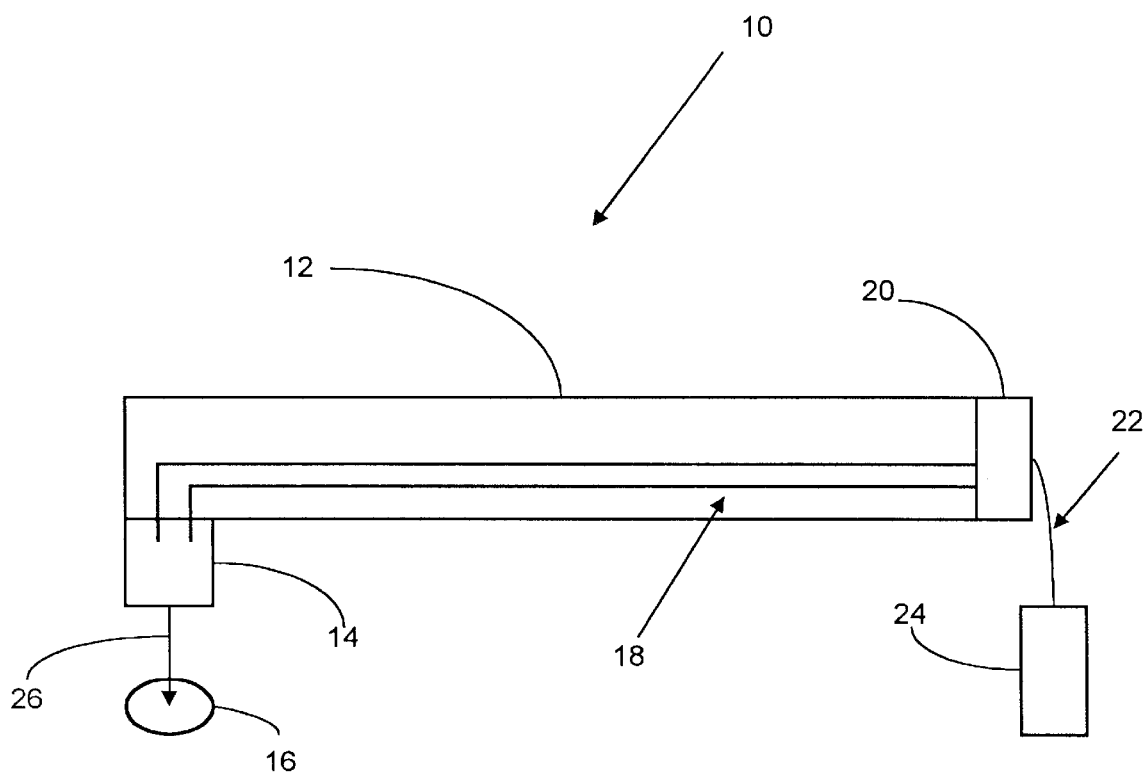
FIG. 1 is a schematic view of an apparatus suitable for performing the dental composition curing method of the present invention using a LED radiation source.

FIG. 1 shows schematically the elements of an dental curing apparatus 10 suitable for performing the dental composition curing method of the present invention using a LED radiation source. The curing apparatus 10 comprises an elongate handle 12 shaped for operator convenience in positioning an light emitting diode (LED) 14 proximate a target dental composition 16 so that curing radiation emitted from the LED 14 is directly incident upon the dental composition target 16. LED 14 may be attached to handle 12 by any of several methods, including clamping, receiving in a recess, gluing and the like. LED 14 is activated by means of a pair of low voltage power wires 18 illustrated for convenience as being contained within handle 12. Wires 18 are joined by means of a suitable connector 20 and power cord 22 to a programmable power supply 24 selected to provide the desired power parameters. When activated, LED 14 irradiates radiation energy, illustrated by arrow 26 onto the target material 16. If desired, a conventional radiation radiometer, not illustrated, may be used to ensure that power output from the LED 14 is within normal operating ranges.

Exemplary LEDs 14 useful in practicing the present invention include Panasonic's "LED Blue Clear" 1500 millicandela T[1] ¾, LNG992CFBW and similar devices commercially available from Hewlett Packhard and Toshiba. Such LEDs emit radiation in the range from about 440 to about 500 nanometers with a power output of about 1500 millicandela. A programmable power supply 24 employed in conjunction with the above identified Panasonic LED is well know in the industry; specifically a model PS 281 produced by Tektronix was to obtain the results described below.

Dental compositions 16 suitable as a filling material for cavities in teeth are well known in the art and may be obtained by mixing liquid phosphoric acid, water and a paste composed of a ceramic and hydroxyapatite, in a proportion to form a suitably workable composition. A typical dental composition has a liquid component of about 40% phosphoric acid in water and a paste component of about 80% ceramic and 20% hydroxyapatite. Increased amounts of hydroxyapatite demand more energy to cure the composition. The ceramic component may be composed of corderite, silica or silicium oxide, or aluminum oxide, for example. The powder components will have the grain sizes normally used for dental filling materials.

The following examples are given to help a complete understanding of this invention and are provided herein for purposes of illustration only and are not intended to be limiting in any manner.

Exemplary Evidences

In order to demonstrate the improved dental curing obtained using LED radiation in accordance with the present invention, comparative tests were completed using the dental curing apparatus 10 as described above and a conventional dental radiation curing unit like that available from Denstsply International Inc., Caulk Division, Milford, Del., specifically the Spectrum™ Curing Unit, Model 200R. This unit is typical of other commercially available conventional curing units and employs a quartz halogen lamp filtered with a blue filter and includes an on-board radiometer to assure minimum levels of output power. The Model 200R provides a minimum operating intensity of about 450 $mW/cm^2$ in the 400–500 nanometer wavelength range at the output of its light guide. This intensity decreases as distance to the target from the output end is increased.

Tests described herein were completed using commercially available dental compositions; in particular, two different products, the DenMat® Marathon V#5474 and the Caulk TPH Spectrum Shade A 3.5 compositions were used to obtain comparative performance data between the LED curing method of the present invention and prior art conventional methods. In all the following exemplary tests, the dental curing apparatus 10 was operated at a energy output level of about 25 $mW/cm^2$ and was stationed at a distance of about 7 mm±2 mm above the dental composition target 16 for a period of 60 seconds. The conventional Spectrum™ 200R Curing Unit was operated at an energy output level of about 300 $mW/cm^2$ at the target 16 for a period of 60 seconds.

(1) Measurement of Depth of Cure

Depth of cure was measured in accordance with the established industry standard depth of cure measurement technique defined by the International Organization for Standardization as ISO DIS 4049; 1998. This technique employs a 7 mm thick stainless steel mold having a 4.0 mm diameter cylinder that extends through the mold. The thickness of the mold is 2 mm greater than twice the maximum depth of cure claimed. The dental composition to be cured, in this instance, the Caulk TPH Spectrum Shade A 3.5 composition, is tightly filled into the cylinder and the open ends of the cylinder are covered with a polyester film. One end of the cylinder is irradiated with curing radiation under test conditions and then the uncured material is removed from the cylinder. The cured cylinder is removed from the mold and the cured height is measured with a micrometer. The depth of cure is recorded as half the height of the cured cylinder and the test is repeated twice. As described above, both radiation sources, the dental curing apparatus 10 and the Spectrum™ 200R Curing Unit were used to cure the cylinder of dental composition.

Depth of cure for a 4 mm diameter cylinder mold was then measured and determined to be 1.5±0.1 mm for the LED radiation curing apparatus 10 at 25 $mW/cm^2$. In contrast, to obtain a similar depth of cure using conventional blue-light radiation like that emitted from the conventional Spectrums™ 200R Curing Unit, it was necessary to operate at a power level of 53 $mW/cm^2$. In the instance of obtaining a 2 mm depth of cure, the LED radiation curing apparatus 10 was operated at 38 $mW/cm^2$ and the conventional blue-light radiation curing gun was operated at about 200 $mW/cm^2$. Thus, the LED curing apparatus 10 may be operated at a much lower irradiation intensity than conventional dental guns to obtain an essentially equivalent or greater depth of cure.

(2) Measurement of Shrinkage

Figure 2:
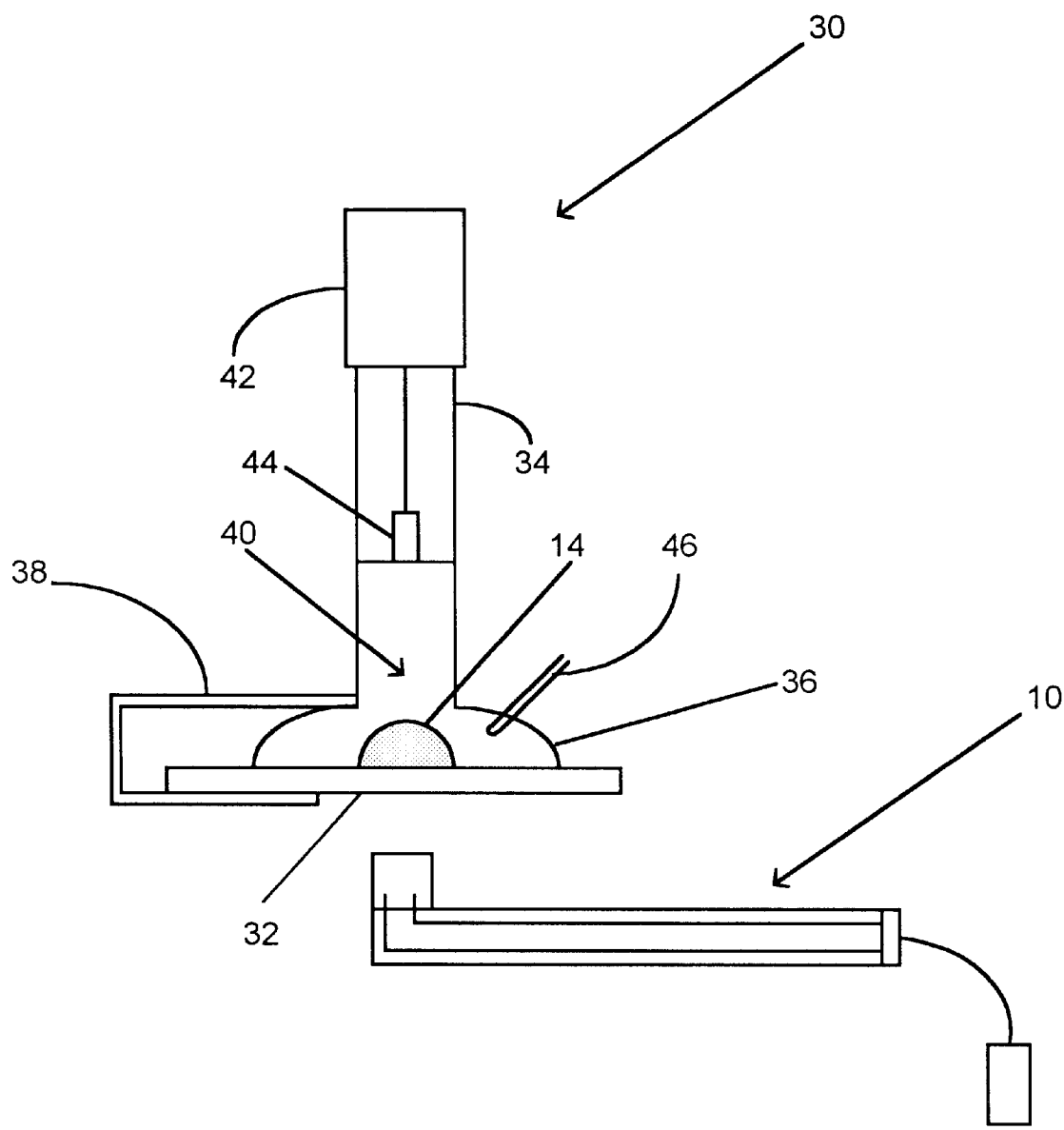
FIG. 2 is a schematic view of a mercury dilatometer testing method suitable for evaluation of shrinkage rate and heating using the LED radiation dental composition curing method of the present invention.

The degree of shrinkage associated with polymerization with a polymer dental composition was measured in accordance with an established ADAHF industry standard technique using a dilatometer 30 like that illustrated in FIG. 2. A dab of dental composition 14 with approximately 0.1 gram mass is placed on a standard microscope slide 32 that has been tared on a 4-digit balance. The composition 14 is spread on the slide 32 with a spatula, keeping the composition less than 1.5 mm thick and less than 5 mm in diameter to assure complete curing. The weight of the composition is recorded to 4 decimals. An open glass measurement tube 34 having a cupshaped end section 36 is positioned with the cup-shaped end section 36 facing upwards and the microscope slide 32 with dental composition 14 is inverted over the cup so that the composition is centered in the cup. The slide 32 is clamped secured to the measurement tube with a clamp 38, rotated 180-degrees to the orientation shown in FIG. 2 and filled with mercury 40. A prescribed linear displacement transducer 42, a Lucas Shaevitz LVDT, assembly is slowly lowered into the tube 34 until it rests on top of the glass measurement tube 34 with its plunger 44 floating on the mercury 40. A prescribed thermistor 46, an Omega 44133 thermistor is built into the cup-shaped section 36 of the measurement tube 34 and positioned to be in contact with the mercury 40 surrounding the composition 14 being tested. The LVDT assembly 42 and the Omega 44133 thermistor 46 are connected to a control box (not shown) and interfaced to a computer (not shown). Both radiation sources, the dental curing apparatus 10 and the conventional Spectrum™ 200R Curing Unit were used to irradiate the dental composition as illustrated in FIG. 2 for 60 seconds at output power levels of 25 $mw/cm^2$ and 300 $mw/cm^2$, respectively.

A software program developed by the ADAHF residing within the computer is used to acquire and analyze data related to an expansion of the mercury from the LVDT and mercury temperature changes registered by the thermistor. The change in mercury level results from two sources: (1) shrinkage in dental composition due to polymerization, and (2) expansion in mercury due to irradiation induced heating. The software program calculates the expansion in mercury from the thermistor temperature data. The overall volume change is calculated based on LVDT data. From the combination of these data, the shrinkage within the dental composition may be calculated once the final density of cured polymer is provided. Final density of the polymer is measured using a Mettler Toledo AT 261 balance in combination with a Mettler Toledo 210485 density determination kit.

(3) Measurement of Heat

The increase in temperature associated with a 60-second exposure for achieving a depth of cure of 1.5 mm was measured using the ADAHF dilatometer described above. Again, both radiation sources, the dental curing apparatus 10 and the conventional Spectrum™ 200R Curing Unit were used to expose dental composition target 16 for 60 seconds at output power levels measured to be 25 mW/cm² for the LED curing apparatus 10 and 450 mw/cm² at the output end of the conventional blue-light dental gun. Due to the relatively high divergence of the conventional dental gun, its 300 mW/cm² output irradiation corresponds to an energy density of about 53 mW/cm² at the dental target 16. In contrast, the energy density of the LED curing apparatus 10 remains about 25 mW/cm² due to the low divergence of the LED beam.

Figure 3:
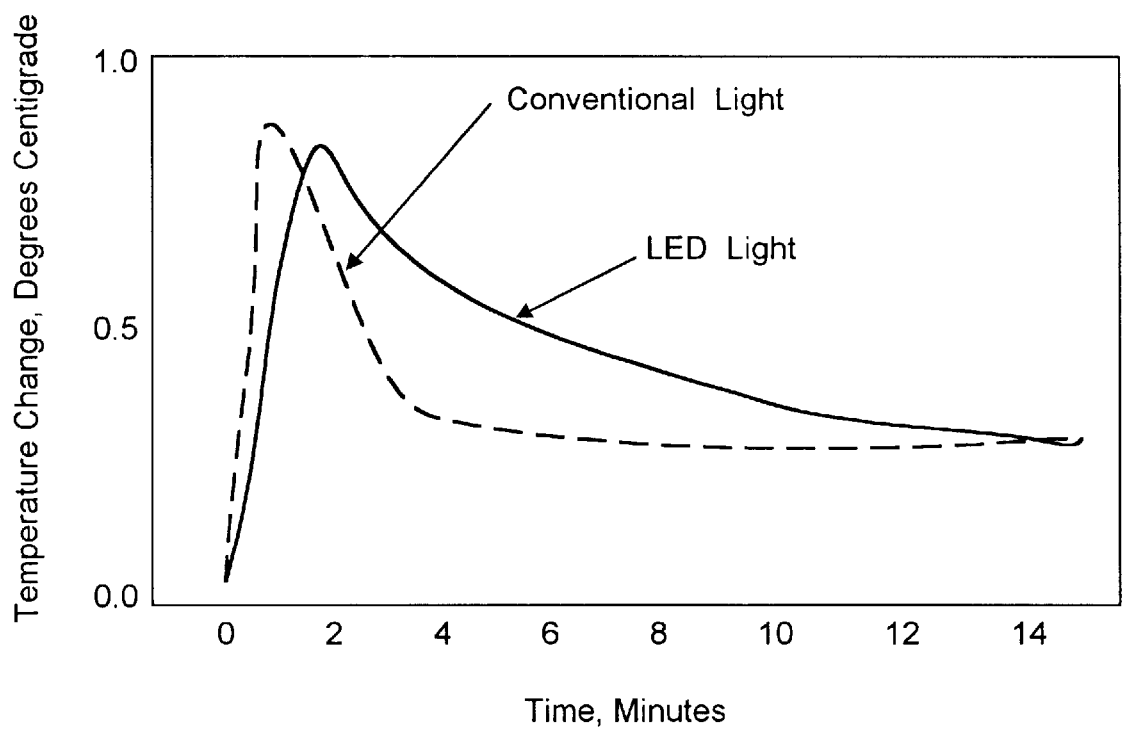
FIG. 3 is a graphical representation of temperature measurements obtained with the dental composition curing method of the present invention using a LED radiation source; and, FIG. 4 is a graphical representation of depth of cure measurements obtained with the dental composition curing method of the present invention using a LED radiation source.

Temperature measurements beginning after the 60-second irradiation period are illustrated in FIG. 3. The dental curing apparatus 10 using an LED 14 illustrated with a solid line produced an initial temperature increase of about 0.78° C. whereas in contrast the conventional light Spectrum™ 200R Curing Unit illustrated with a dashed line produced an initial temperature increase of about 0.85° C. Thus the dental curing apparatus 10 produced lower overall heating of the composition in contrast to the higher overall heating from the conventional blue light curing unit. Thereby, when treated with the dental curing method of the present invention, a patient will experience a significantly lower degree of discomfort as a result of the about 8% lower temperatures during curing of an embedded dental composition.

Shrinkage measurements made using these same irradiation intensities as in FIG. 3, which yield a 1.5 mm depth of cure, showed that the dental curing apparatus 10 of the present invention operating at 25 mw/cm² produced a shrinkage of 2.758% whereas in contrast the conventional Spectrumm 200R Curing Unit operating at 53 mW/cm² produced a shrinkage of about 2.960%. This is a net shrinkage reduction of about 7% when using the inventive dental curing method and apparatus 10, a strongly desirable advantage of the present invention.

(4) Failure Mode

Although actual results were not experimentally determined, it is well known within the industry that dental curing guns employing conventional radiation sources gradually lose power output during the life of the dental gun. For example, a negative correlation between the depth of cure and the age of light-curing guns has been reported, with older Heliotests (Ivoclar-Vivadent) units tending to cure a Z100 Composite (3M) dental composition to less depth than newer units [Prim Dent Care September 1997;4 (3):91–4]. Because of this time loss of power output, curing lights are considered as unsuitable for use with a reading of less than 200 mw/cm² using a curing radiometer and greater than 50 mw/cm² using a heat radiometer [J Dent March 1999;27(3):235–41] underscoring the necessity of monitoring the output of conventional dental curing guns as they age in use. In contrast, an inherent characteristic of LED radiation sources like those used in the present invention is a stable level of output radiation during the operating life of a LED, with a catastrophic failure that is readily noticeable by an operator whenever the output declines.

(5) Relative Costs

The expenses associated with conventional radiation dental curing guns comes about as a result of the need to provide relatively high output power with appropriate filtering and cooling means. Such guns and the associated power supply cost in the $600–1,000 range. In contrast, the LED-base dental curing method of the present invention employs low power LEDs costing in the $2 range and not requiring the high output power, filtering and cooling means of conventional dental curing guns.

In the way of summary, the following Table contains the results of the Examples in a condensed form. The advantages of using the present invention are evident and furthermore are totally unexpected in view of the absence within prior art of the use of LEDs for effective curing of dental compositions.

TABLE 1

| Radiation Source | Blue Clear LED | Filtered Quartz Halogen |
|---|---|---|
| Depth of Cure | 2 mm for 38 mW/cm² at the dental composition target | 2 mm for 200 mW/cm² at the dental composition target |
| Temperature Increase for a 1.5 mm depth of cure | About 0.78° C. | About 0.85° C. |
| Shrinkage for a 1.5 mm depth of cure | 2.758% | 2.960% |
| Failure Mode | Catastrophic in time | Slow deterioration in time |
| Relative Cost of Light | About $2 | About $100 |
| Beam Divergence | 6 degrees | 27 degrees |

Figure 4:
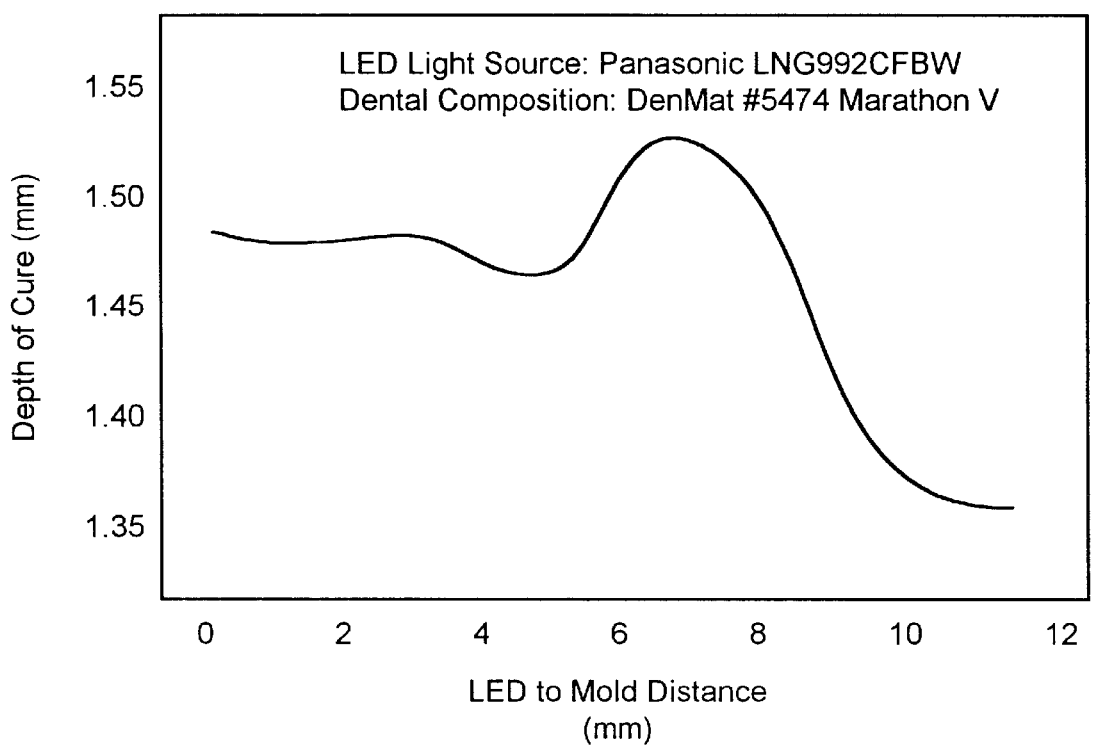

It is to be understood that the embodiments of the invention disclosed herein are illustrative of the principles of the invention and that other modifications may be employed which are still within the scope of the invention. For example, in one alternate exemplary embodiment, a dental composition having a different formulation from the one in the Evidences may be employed. It is known from the literature that Axis and Thermoresin LC II dental compositions may be cured with both UV and visible radiation while another composition Dentacolor is cured substantially by visible light [J Oral Rehabil October 1998;25(10): 770–5]. To confirm the effectiveness of the present invention, the depth of cure of a second commercially available dental composition known as Marathon V available from Den-Mat® was also evaluated using the LED-based curing method of the present invention in the aforedescribed ISO DIS 4049 testing method. The test results were essentially a duplicate of those reported in the above Evidences, part (1), and are shown in FIG. 4 thereby confirming the broad applicability of the present invention in curing dental compositions that are known to be curable by the application of radiaton. FIG. 4 illustrates the depth of cure as a function of the distance of the LED from the dental composition with a blue-light Panasonic LED with a curing time of 60 sec. FIG. 4 shows that using the present inventive method provides a relatively constant depth of cure as long as the LED is positioned within a distance of 8 mm from the dental composition, a result of the low divergence of the LED beam in comparison to the highly divergent radiation generated within a conventional filtered light dental gun. Optimum distance from the dental composition target is seen to be in the range of 1–8 mm for the LED curing apparatus 10.

In another alternate exemplary embodiment, it is obvious that a light emitting diode having other than "clear blue" wavelengths may be employed as long as the dental composition may be cured by the application of corresponding radiation. It is known from the literature that microfilled and hybrid composition materials designed for prosthetic veneer may be cured with different types of light, in particular both xenon light and metal halide light sources. Depending on the choice of light source and the choice of dental composition, an increased exposure duration increases the depth of cure for all combinations [J Oral Rehabil May 1998; 25 (5):348–52]. Accordingly the present invention may be practiced using any LED having its wavelength selected to provide radiation energy in the effective curing range for the composition being employed. In this alternate exemplary embodiment, the duration of radiation exposure with a LED as disclosed in the present application may be increased to accomplish a minimum acceptable depth of cure, depending on the selection of LED radiation wavelength and the selection of dental composition. Accordingly, the present invention is not limited to those embodiments precisely shown and described in the specification but only by the following claims.

What is claimed is:

1. A method for curing a dental composition suitable for repairing a dental cavity or a dental surface comprising:

applying the dental composition to the cavity or surface; and, exposing the composition to radiation from a light emitting diode having output wavelengths selected to photo-activate a hardening chemical reaction within the composition, wherein the light emitting diode is operated at a power output in the range of about 25 mW/cm$^2$ to about 38 mW/cm$^2$, wherein the dental composition comprises a photo-curable composition, the light emitting diode is positioned a distance of about 7 mm±2 mm from the dental composition, and wherein a depth of cure of about 3 mm is achieved.

2. A method for curing a dental composition suitable for repairing dental cavities or dental surfaces by applying the dental composition to an affected area and exposing the composition to radiation from a single light emitting diode, wherein the dental composition comprises a photo-curable composition and the light emitting diode is operated for about 60 seconds at a power output of about 20 mw/cm$^2$ at a distance of about 7 mm from the dental composition so that a depth of cure of about 3 mm is achieved.

* * * * *